United States Patent [19]
Ochs

[11] Patent Number: 5,588,689
[45] Date of Patent: Dec. 31, 1996

[54] DENTAL INSTRUMENT HOLDER

[76] Inventor: Eric W. Ochs, 22448 Hoffman, St. Clair Shores, Mich. 48082

[21] Appl. No.: 418,202

[22] Filed: Apr. 7, 1995

[51] Int. Cl.⁶ ............................... B25B 7/00; B25J 15/00
[52] U.S. Cl. ............................................. 294/118; 294/16
[58] Field of Search ........................... 294/7, 8, 8.5, 11, 294/16, 28, 29, 31.1, 50.8, 99.2, 106, 117–119; 433/229

[56] References Cited

U.S. PATENT DOCUMENTS

| | | | |
|---|---|---|---|
| 72,275 | 12/1867 | Euteneuer | 294/118 |
| D. 90,137 | 6/1933 | Gutsche | 294/8.5 X |
| 1,095,054 | 4/1914 | Wiesenfeld | 294/118 |
| 1,149,476 | 8/1915 | Thebert | 294/118 |
| 1,569,999 | 1/1926 | Nelson | 294/8.5 |
| 1,787,331 | 12/1930 | Wilson | 294/118 |
| 2,016,356 | 10/1935 | Alberg . | |
| 2,219,558 | 10/1940 | Jacobson | 294/118 |
| 2,279,809 | 4/1942 | Apfel . | |
| 2,507,368 | 5/1950 | Carlson . | |
| 2,643,151 | 6/1953 | Zupancic | 294/118 |
| 2,743,726 | 5/1956 | Grieshaber | 294/118 X |
| 2,789,006 | 4/1957 | Mattson | 294/118 |
| 2,915,333 | 12/1959 | Koenig et al. . | |
| 2,997,326 | 8/1961 | Daum . | |
| 3,384,407 | 5/1968 | Thrash . | |
| 3,560,039 | 2/1971 | Gruber . | |
| 4,109,952 | 8/1978 | Monzain . | |
| 4,186,956 | 2/1980 | Flynn . | |
| 5,054,226 | 10/1991 | Hart | 294/16 X |

*Primary Examiner*—Johnny D. Cherry
*Attorney, Agent, or Firm*—Young & Basile, PC

[57] ABSTRACT

A holder retains a plurality of dental instruments used in a single dental procedure together in a separate group during cleaning and prior to sterilization. The holder includes first and second pivotally connected, opposed tong members, each formed of a handle portion and a jaw lever portion. Each jaw lever portion includes a cross arm extending laterally from the handle portion and terminating in a pair of arcuate shaped jaws at outer ends of each cross arm. The jaws in one tong member concavely oppose the jaws in the opposite tong member to form the closed opening between the jaws when the first and second tong members are moved to one of a plurality of separate closed positions. The first and second tong members are pivotally connected together and include a lock which enables the opposed jaws of each of the first and second tong members to be disposed in one of a plurality of discrete positions forming variably selectable, different sized openings between the opposed jaws to securely receive a particular number of dental instruments therebetween.

8 Claims, 4 Drawing Sheets

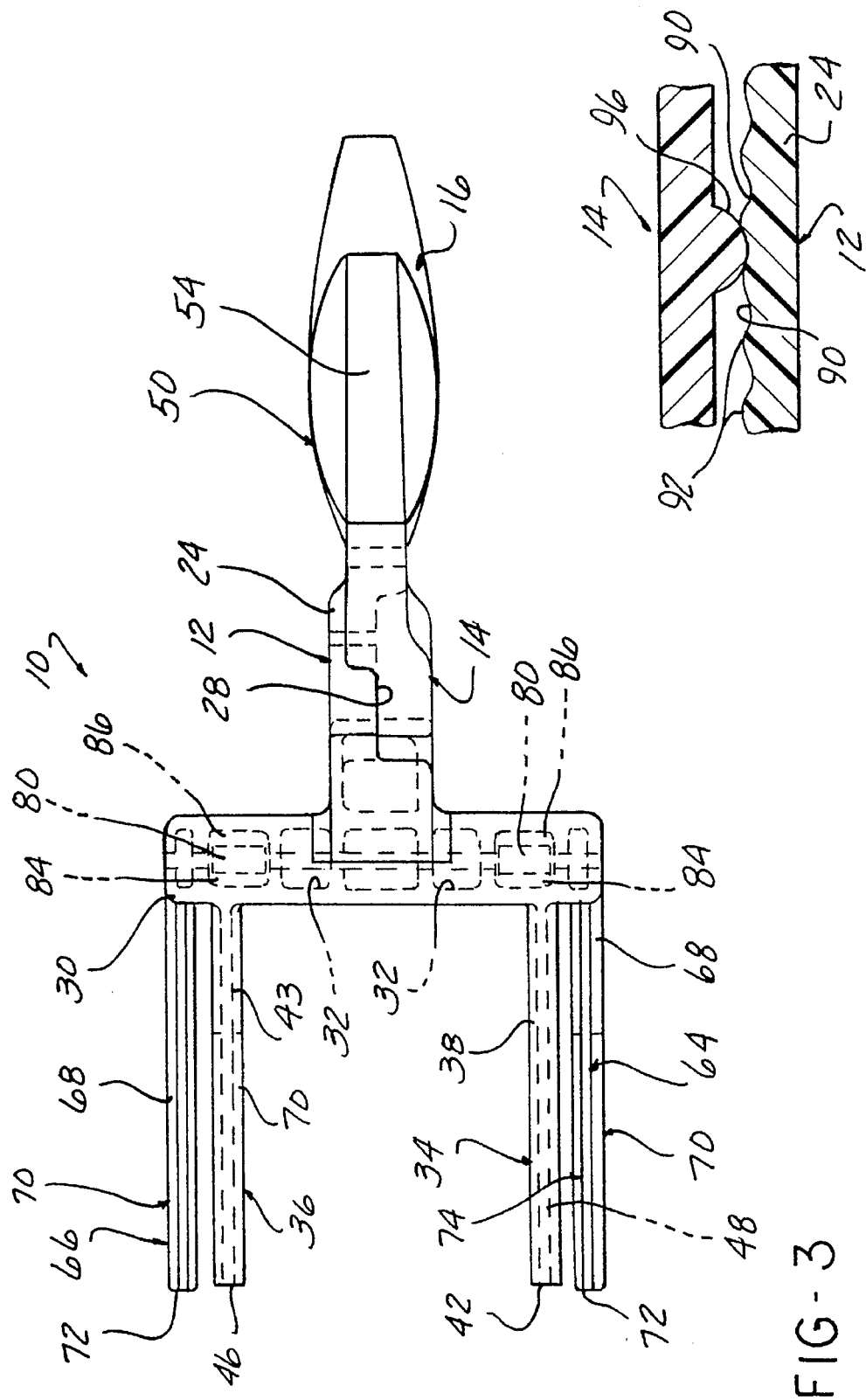

DENTAL INSTRUMENT HOLDER

BACKGROUND OF THE INVENTION

1. Field of the Invention

The present invention relates, in general, to dental instruments and, more specifically, to apparatus for holding dental instruments during cleaning and prior to sterilization.

2. Background Description

Different dental instruments are used by dentists and dental hygienists in performing various dental procedures, such as cleaning, filling, crown emplacement, extractions, etc. Such instruments, which include scalers, carvers, mirrors, explorers, mixing instruments, etc., to name a few, generally have an elongated handle of small diameter with an appropriately shaped tool mounted on one or both ends of the handle.

Certain types of dental instruments are always used in group to perform a particular dental procedure, such as three different instruments used for examination and cleaning, four or five instruments for crown preparation and mounting, and approximately ten instruments for placing a filling in a tooth.

After use, the dental instruments are placed in a basket in an ultrasonic cleaner for gross cleaning and then inserted into an autoclave for sterilization prior to reuse. However, it is common, particularly in dental offices with several dentists and/or hygienists, to intermix a number of groups of dental instruments in the ultrasonic cleaner as a single, large group. After cleaning, the instruments are then hand sorted into the particular dental procedure group, placed in sealable bags containing one complete group of instruments, and then inserted into an autoclave for sterilization. This is a time consuming task and requires additional handling of the cleaned and sterilized instruments.

To eliminate the sorting of groups of dental instruments used in a particular dental procedure from the large intermixed group of instruments removed from the ultrasonic cleaner after sterilization, it is known to use a flexible tie around each group of dental instruments used in a particular dental procedure. The instruments in the bag are then routed through the ultrasonic cleaning step while being retained in a particular dental procedure group. While the use of such ties eliminates sorting of particular instruments from a large intermixed group of instruments, each group of instruments is still handled by hand during rinsing, drying and placement in bags for sterilization.

Thus, it would be desirable to provide a dental instrument holder which is designed to separately hold one group of instruments used in a particular dental procedure during ultrasonic cleaning of such instruments. It would also be desirable to provide such a dental instrument holder which is adjustable in size for use in holding a different number of dental instruments used in different dental procedures. Finally, it would be desirable to provide such a dental instrument holder which can be easily reused, is not easily susceptible to breakage, does not interfere with the ultrasonic cleaning of the dental instruments and eliminates hand contact with the instruments.

SUMMARY OF THE INVENTION

The present invention is a dental instrument holder capable of holding a group of varying numbers of dental instruments used in a single dental procedure during cleaning and prior to sterilization of such instruments.

The dental instrument holder includes first and second tong members, each including a jaw lever portion and an opposed handle portion. The first and second tong members are pivotally connected for movement of the jaw lever portions between opened and closed positions.

Each jaw lever portion of the first and second tong members includes first and second jaws interconnected by a laterally extending cross arm. In a preferred embodiment, the first and second jaws on the first tong member are spaced laterally apart at a different spacing than the first and second jaws of the second tong member so as to dispose opposed first and second jaws on the first and second tong members in a side-by-side relationship. Preferably, the first and second jaws on the first tong member are spaced closer together than the first and second jaws on the second tong member.

Each of the first and second jaws on the first and second tong members has an arcuate shape with the first and second jaws on the first tong member concavely opposing the first and second jaws on the second tong member to form a variably selectable sized opening between each first and second jaw pair.

Preferably, the outer ends of each of the first and second jaws on each of the first and second tong members extend past the outer ends of the opposed jaw of each jaw pair to close the opening formed between mating jaws. This arrangement coupled with the side-by-side position of the first and second jaws on each of the first and second tong members provides a closed variable selectable sized opening which is capable of receiving and securely holding different numbers of dental instruments depending on the opening size.

Pivot means preferably comprises at least one pin mounted on the cross arm of one of the first and second jaw levers. Pin receiving means are mounted on the other of the first and second jaw levers to pivotally receive the pin to provide for pivotal connection of the first and second tong members.

Means are provided for locking the jaw lever portions together to form a variably selectable sized opening between opposed jaw lever portions. The locking means preferably comprises a projection formed on the handle portion of one of the first and second tongs. A plurality of spaced projection receiving grooves are formed in the handle portion of the other of the first and second tong members and slidably receive the projection therein. As the first and second tong members are preferably formed of a slightly resilient plastic material, the projection is easily slidable across the grooves into fixed engagement with a selected groove to enable a particular sized opening to be formed between the opposed jaw pairs to securely receive a desired number of dental instruments between the jaw pairs.

The dental instrument holder of the present invention provides unique advantages during cleaning of dental instruments. The present dental instrument holder is designed to hold a single group of dental instruments used in a particular dental procedure as a distinct, separate group during cleaning and prior to sterilization of the instruments. This eliminates the need for sorting a group of dental instruments used in a particular procedure from a large number of instruments typically placed in ultrasonic cleaners. The dental instrument holder is easily operable and can be locked in a number of distinct closed positions to provide a variable sized opening between the opposed jaws to receive differing numbers of dental instruments therein. The size of the opening between opposed jaws can be varied according to the number of dental instruments in a group. The dental instrument holder is formed of a plastic material for a reliable, long term use. Finally, the holder eliminates hand contact with the cleaned instruments after cleaning and during insertion of the cleaned instruments into a bag for sterilization.

BRIEF DESCRIPTION OF THE DRAWINGS

The various features, advantages and other uses of the present invention will become more apparent by referring to the following detailed description and drawing in which:

FIG. 3 is plan view of the dental instrument holder depicted in FIG. 2;

FIG. 6 is a cross sectional view generally taken along line 6—6 in FIG. 2;

DESCRIPTION OF THE PREFERRED EMBODIMENT

Figure 1:
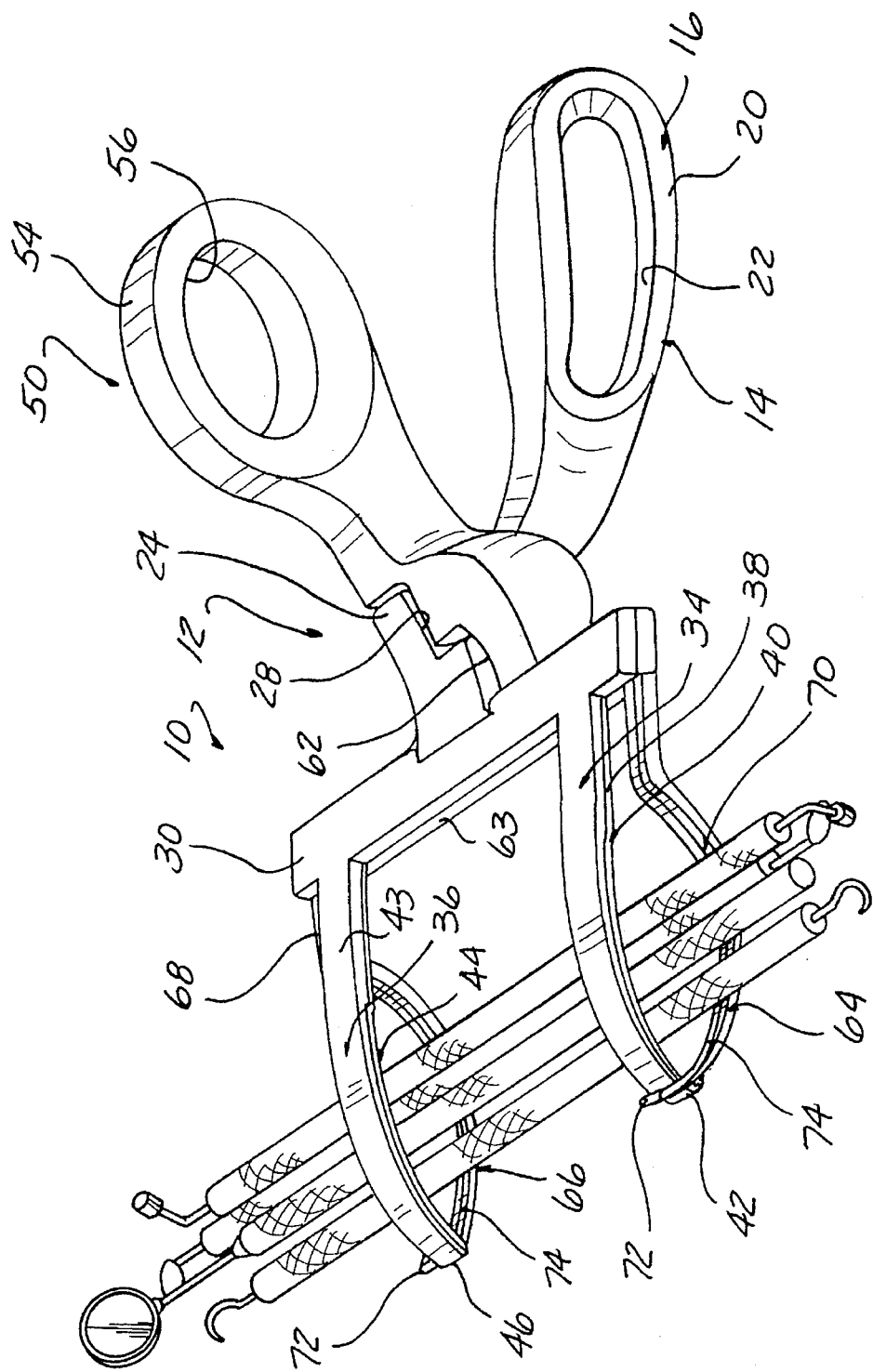
FIG. 1 is a perspective view of a dental instrument holder constructed in accordance with the teachings of the present invention.
Figure 2:
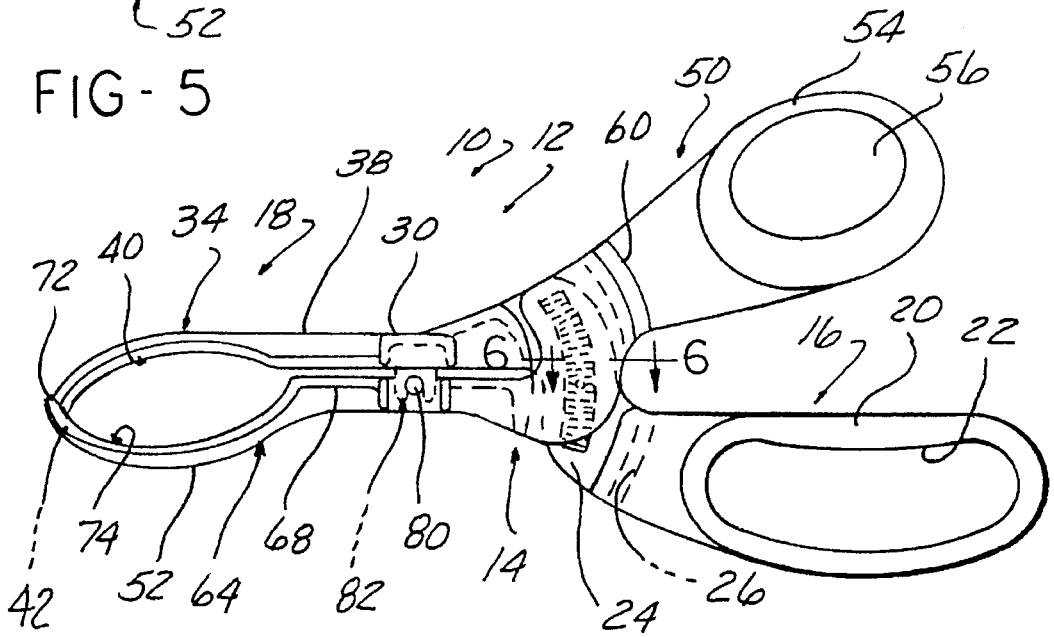
FIG. 2 is a side elevational view of the dental instrument holder depicted in FIG. 1, shown in one of a plurality of distinct closed positions.

Referring now to the drawing, and to FIGS. 1, 2 and 3 in particular, there is depicted a dental instrument holder 10 constructed in accordance with the teachings of the present invention. The dental instrument 10 is designed to receive and securely hold a group of dental instruments, which may contain any number of dental instruments used in a single dental procedure, such as cleaning, examination, filling, crown preparation and cementation, during ultrasonic cleaning. The dental instrument holder 10 includes first and second tong members 12 and 14, respectively, which are generally disposed in an opposed arrangement. As shown in FIGS. 1, 2 and 3, and further in FIG. 4, the first tong member 12 includes an integrally formed handle portion 16 and jaw lever portion 18.

The first and second tong members 12 and 14 may be formed of any suitable material which is capable of withstanding the high temperatures employed in sterilizing dental instruments, such as the high temperatures generated in an autoclave. Preferably, the first and second tong members 12 and 14 are formed of a slightly resilient, plastic material such as a thermoplastic polyetherimide with good dimensional stability. Examples of suitable materials are commercially available from General Electric Company under the ULTEM trademark.

The handle portion 16 includes a closed loop 20 having an aperture 22 formed therein. The aperture 22 is sized to receive two or more fingers, such as the index and one or more additional fingers of a user's hand.

A connector portion 24 extends from one end of the loop 20 to the jaw lever portion 18. The connector portion 24 has a smoothly curved shape as shown in detail in FIG. 4. An arcuate shaped groove 26 is formed in the connector portion 24, the purpose of which will become more apparent hereafter. As shown in FIG. 3, the connector portion 24 includes a lateral offset 28 which is disposed side-by-side with a corresponding offset formed in the second tong member 14 as also described hereafter.

Figure 4:
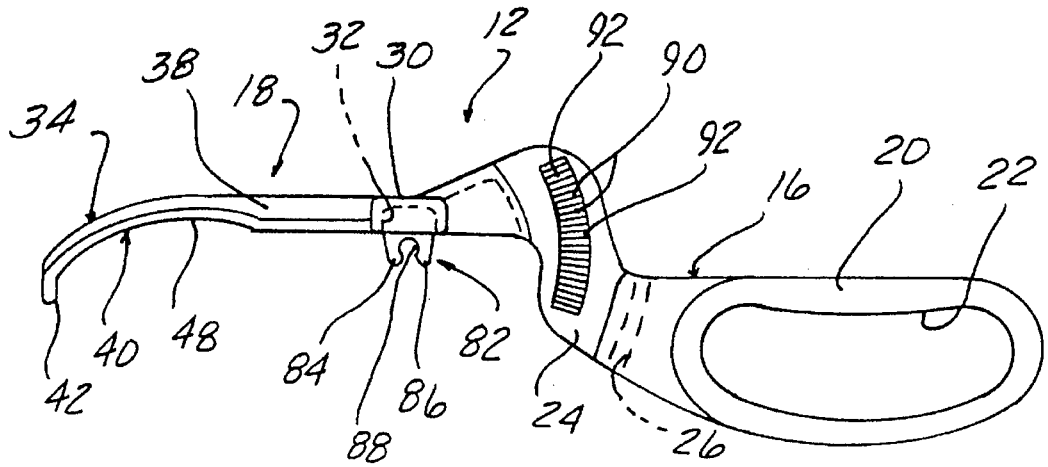
FIG. 4 is a side elevational view of the first tong member shown in FIG. 1 and 2.

The first jaw lever portion 18 of the first tong member 12 includes a laterally extending cross arm 30 which extends integrally from the connector portion 24. Recessed cavities 32 are formed in the cross arm 30 for weight reduction. First and second jaws 34 and 36 extend outward from opposite ends of the cross arm 30, each generally parallel to the handle portion 16 of the first tong member 12. Each of the first and second jaws 34 and 36 is identically constructed and includes a straight leg portion 38, and an arcuate shaped portion 40 which terminates in a depending outer end 42. The second jaw 36 is similarly formed with a straight leg portion 43 extending from the cross arm 30, an arcuate portion 44 and an outer end or tip 46. A narrow edge or ridge 48 extends centrally along the leg 38 and the arcuate portion 40 to the tip 42 of the first jaw 34. The side walls of the first jaw 34 extend angularly outward from the edge 48 as shown in FIGS. 3 and 4. The edge 48 forms an instrument engaging surface as described hereafter. A similar edge 48 is formed on the second jaw 36.

In a normal use position, the jaw lever portion 18 of the first tong member 12 is disposed upper most above the corresponding jaw portion of the second tong member 14. In this orientation, the arcuate portions 40 and 44 of the first and second jaws 34 and 36, respectively, have a concave shape such that the outer ends 42 and 46 of the first and second jaws 34 and 36, respectively, extend away from the corresponding legs 38 and 43 of the first and second jaws 34 and 36.

Figure 5:
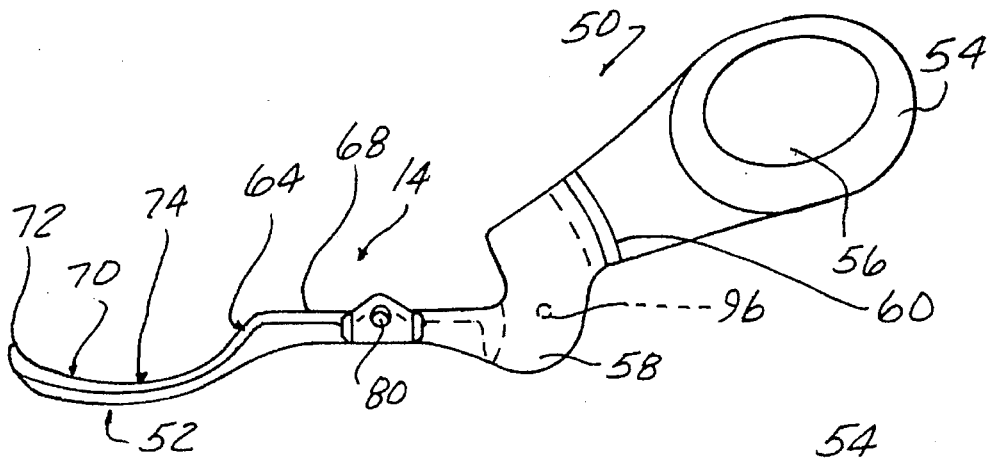
FIG. 5 is a side elevational view of the second tong member shown in FIGS. 1 and 2.

The second tong member 14 is of generally similar construction and includes an integrally formed handle portion 50 and a jaw lever portion 52. The handle portion 50 is formed with a loop 54 having an aperture 56 formed therein sized to receive a user's thumb. A connector portion 58 extends from the handle 50 to the jaw lever portion 52. An outwardly extending arcuate shaped projection 60, as shown in detail in FIGS. 2 and 5, is formed on the handle portion 50 and slidably engages the groove 26 formed in the handle portion 16 of the first tong member 12 to guide the opposed sliding movement of the first and second tong members 12 and 14 relative to each other.

The connector portion 58 includes a lateral offset 62 which slidingly mates with the offset 28 formed in the first tong member 12 to dispose the connector 58 of the second tong member 14 adjacent to the connector portion 24 of the first tong member 12 as shown in FIGS. 1 and 3.

A laterally extending cross arm 63 is integrally formed on and extends perpendicularly from the connector 58 of the second tong member 14. First and second jaw members 64 and 66, respectively, are formed on and extend outward from opposite ends of the cross arm 63. The first and second jaws 64 and 66 are identically constructed and each includes a first straight leg portion 68 extending from the cross arm 63 and an arcuate shaped portion 70 which terminates in an outer tip or end 72. The arcuate portion 70 of each of the first and second jaws 64 and 66 of the second tong member 14 has a concave shape and includes an edge 74 and angularly extending walls which extend from the edge 74 to the sides of each of the first and second jaws 64 and 66.

In the normal use position shown in FIGS. 1 and 2, the arcuate portions 70 of the first and second jaws 64 and 66 of the second tong member 14 have a concave shape opposing the concave shape of the complementary arranged first and second jaws 34 and 36 of the first tong member 12. Further, the first and second jaws 64 and 66 are spaced farther apart than the first and second jaws 34 and 36 of the first tong member 12 so as to dispose the first and second jaws 64 and 66 of the second tong member 14 laterally outward of the complementary first and second jaws 34 and 36 in a side-by-side arrangement as shown in FIGS. 1 and 3. This forms a variably selectable sized opening between the oppositely formed concave portions of the first jaws 34 and 64 and the second jaws 36 and 66. The outer ends of the jaws can pivot past the outer end of the opposed jaw thereby expanding or decreasing the size of the opening between each pair of jaws.

Figure 7:
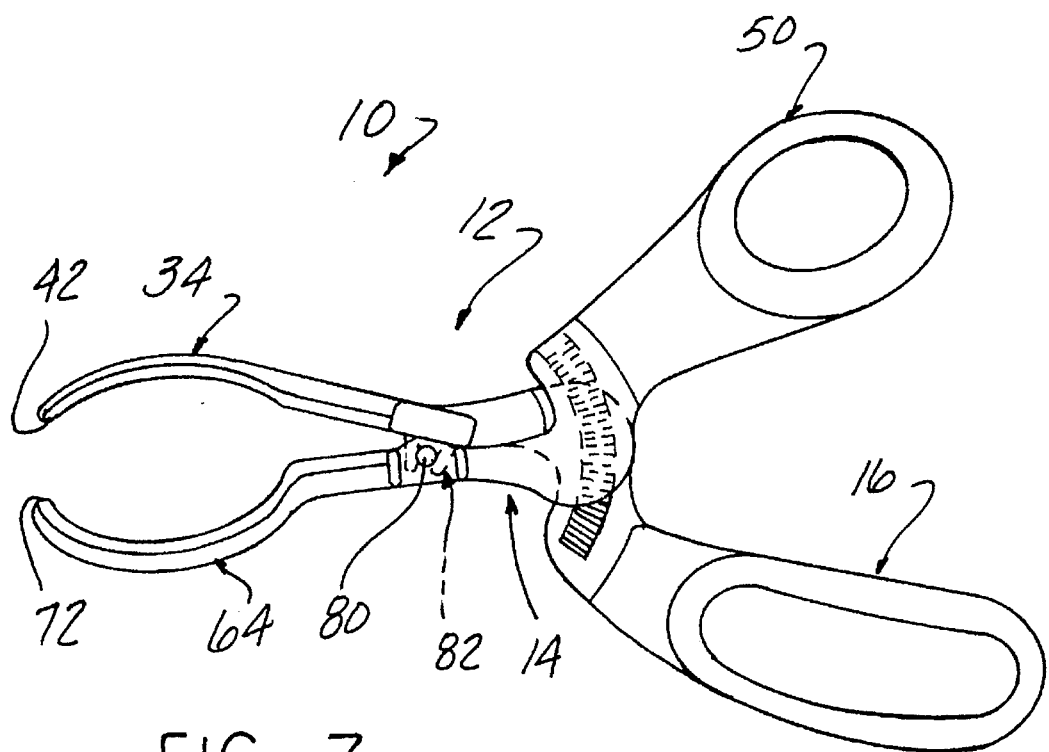
FIG. 7 is a side elevational view showing the dental instrument holder in an open, dental instrument insertion or removal position.
Figure 8:
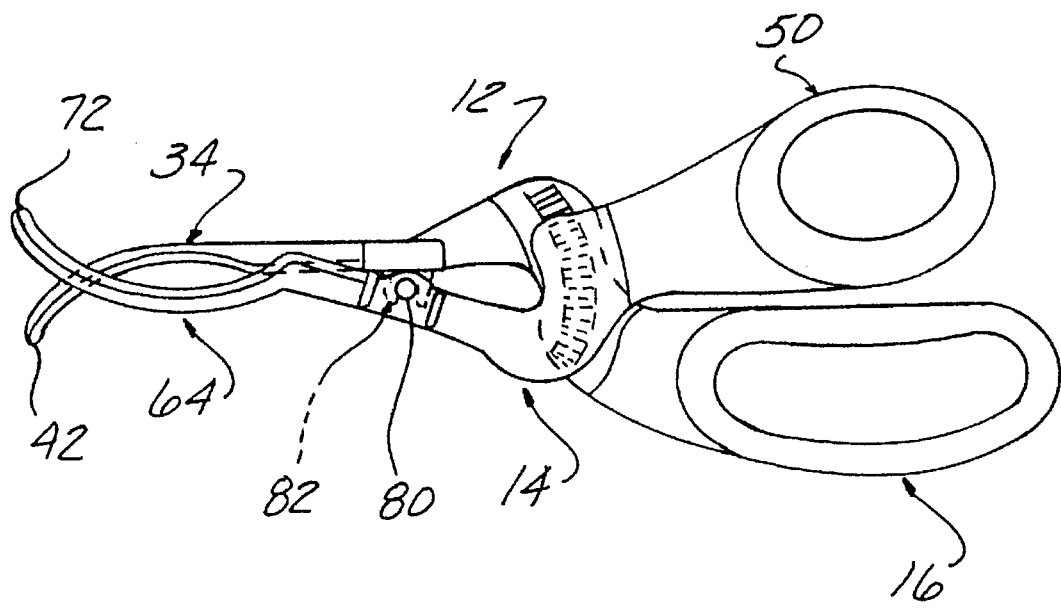
FIG. 8 is a side elevational view showing the dental instrument holder in a closed position different from the position depicted in FIG. 2.

Means are provided for pivotally interconnecting the first and second tong members 12 and 14 together for pivotal movement between an open position shown in FIG. 7 and one of a plurality of distinct closed positions, two of which are shown in FIGS. 2 and 8. The pivot means includes at least one and preferably two spaced pins 80 formed in apertures in the cross arm 63 of the second tong member 14. Pin receiving means denoted generally by reference number 82 are formed on the cross arm 30 of the first tong member 12. The pin receiving means 82 preferably comprises two depending, U-shaped members, each having a pair of spaced legs 84 and 86 and an arcuate shaped slot 88 formed therebetween. The slot 88 has a narrow throat or first end portion between the ends of the legs 84 and 86 and an enlarged diameter inner portion sized to rotatably receive the pin 80. The narrow throat section enables the pin 80 on the second tong member to be forcibly urged through the slot 88 to connect the first and second tong members 12 and 14 together while still providing for pivotal movement of the first and second tong members 12 and 14 relative to each other.

The dental instrument holder 10 also includes lock means for lockingly positioning the first and second tong members 12 and 14 relative to each other in one of a plurality of distinct closed positions in which the arcuate portions of the complimentarily disposed first jaws 34 and 64 and the second jaws 36 and 66 form different sized openings therebetween for securely receiving different numbers of dental instruments. The locking means, in a preferred embodiment, includes a plurality of spaced grooves 90 formed between outwardly extending projections 92 integrally mounted on the connector portion 24 of the first tong member 12 as shown in FIGS. 2 and 4, and in detail in FIG. 6. The grooves 90 are disposed in an arcuate arrangement as shown in FIGS. 2 and 4 and correspond to the pivotal movement of the first and second tong members 12 and 14 relative to each other.

The lock means also includes an outwardly extending projection 96 formed on the connector portion 58 of the second tong member 14 which slidably engages and locks in a selected one of the grooves 90 on the first tong member 12. As the grooves 90 and projections 92 preferable have a smoothly curved shape, as shown in FIG. 6, the arcuate shaped projection 96 can easily slide across the projections 92 for engagement in a selected one of the grooves 90. This easy sliding movement enables the first and second tong members to be moved from an open, dental instrument receiving or removing position shown in FIG. 7 upon outward pivotal movement of the handle portion 16 and 50 of the first and second tong members 12 and 14 away from each other to one of a plurality of closed positions, two of which are shown in FIGS. 2 and 8, to securely receive a number of different dental instruments between the opposed jaw pairs 34, 64 and 36, 66 when the handle portions 16 and 50 are pivoted toward each other. During such closing movement of the handle portions 16 and 50 toward each other, the projection 96 slides across the grooves 90 into fixed engagement with one of the grooves 90 selected by the user depending upon the number of dental instruments contained between the jaw pairs 34, 64 and 36, 66. Due to the slightly resilient nature of the material forming the first and second tong members 12 and 14, the projection 96 is held in engagement with the selected groove 90 to retain the jaw pairs 34, 64 and 36, 66 in a locked position.

After the dental instruments have been inserted between the jaws 34, 64 and 36, 66, and the first and second tongs 12 and 14 move to the desired closed position in which the jaws 34, 64, 36, 66 fixedly engage the group of dental instruments disposed therebetween, the entire dental instrument holder 10 may be placed in an ultrasonic cleaner for gross cleaning of the dental instruments. After ultrasonic cleaning, the holder 10 is used to hold the instruments during rinsing and drying and to insert the group of instruments into a sealable bag for placement in an autoclave for sterilization of the dental instruments, all without hand contact with the instruments. During the cleaning process, the dental instrument holder 10 securely holds the dental instruments mounted therein in a discrete group. As the group of dental instruments are typically used in a single dental procedure, such as filling, crown preparation and cementation, examination, etc., the group of dental instruments are retained in the desired grouping thereby eliminating any subsequent sorting of dental instruments used in a particular dental procedure from a large number of intermixed instruments used in a variety of dental procedures. The dental instrument holder of the present invention is formed of a resilient plastic for a long term, reliable use. Importantly, the dental instrument holder eliminates hand contact with the dental instruments during the entire cleaning process and including the step of inserting the cleaned instruments into a sealable bag used in autoclave sterilization.

What is claimed is:

1. A dental instrument holder for releasibly holding at least one elongated, rigid dental instrument having opposed ends, the holder comprising:

first and second tong members, each including a jaw lever portion and an opposed handle portion;

means for pivotally connecting the first and second tong members for opposing pivotal movement;

each jaw lever portion including only first and second spaced jaws interconnected by a cross arm integrally extending from the handle portion;

at least one of the first and second jaws on the first and second tong members having an arcuate concave shape extending from the cross arm to an outer end; and the first and second jaws on the first tong member spaced apart at a different spacing from the first and second jaws on the second tong member to dispose the first jaws and the second jaws on the first and second tong members in respective side-by-side relationship, with the outer ends of each first and second jaw pivoted beyond the outer end of the opposed first and second jaw to form a variably sized closed opening between the first and second jaws for supporting the opposed first and second ends of the at least one dental instrument.

2. The dental instrument holder of claim 1 wherein:

the first and second jaws on the second tong member are spaced closer together than the first and second jaws on the first tong member.

3. The dental instrument holder of claim 1 wherein the pivotally connecting means comprises:

at least one pin mounted on the cross arm of one of the jaw lever portion of the first and second tong members; and pin receiving means, mounted on the other of the first and second jaw lever portions, for pivotally receiving the pin therein.

4. The dental instrument holder of claim 1 further comprising:

means for locking the first and second tong members in one of a plurality of discrete closed positions in which complimentary arranged first jaws and complimentary arranged second jaws are disposed at selectable spacings to form a selectable sized aperture between the opposed first jaws and the opposed second jaws.

5. The dental instrument holder of claim 4 wherein the locking means comprises:

a projection formed on and extending outward from one of the first and second tong members; and a plurality of spaced projection receiving grooves formed in the other of the first and second tong members, the grooves lockingly receiving the projection to lock the jaw lever portions of the first and second tong members in one of plurality of distinct closed positions.

6. The dental instrument holder of claim 1 wherein:

the first and second jaws of each of the first and second tong members have concave, arcuate shape, the first and second jaws of the first tong member concavely opposing the first and second jaws of the second tong member.

7. The dental instrument holder of claim 1 wherein:

each of the first and second jaws on each of the first and second tong members has a narrow ridge projecting outwardly from opposed, facing spaced sides of each of the first and second jaws.

8. A dental instrument holder for releasibly holding at least one elongated, rigid dental instrument having opposed ends, the holder comprising:

first and second tong members, each including a jaw lever portion and an opposed handle portion;

means for pivotally connecting the first and second tong members for opposing pivotal movement;

each jaw lever portion including only first and second spaced jaws interconnected by a cross arm integrally extending from the handle portion;

at least one of the first and second jaws on the first and second tong members having an arcuate concave shape extending from the cross arm to an outer end;

the first and second jaws on the first tong member spaced apart at a different spacing from the first and second jaws on the second tong member to dispose the first jaws and the second jaws on the first and second tong members in respective side-by-side relationship with the outer ends of each first and second jaw pivoted beyond the outer end of the opposed first and second jaw;

means for locking the first and second tong members in one of a plurality of discrete closed positions in which complimentary arranged first jaws and complimentary arranged second jaws are disposed at selectable spacings to form a selectable sized aperture between the opposed first jaws and the opposed second jaws for supporting the opposed ends of the at least one dental instrument.

* * * * *